United States Patent [19]
Perttunen et al.

[11] Patent Number: 5,968,728
[45] Date of Patent: Oct. 19, 1999

[54] MOLECULAR DETECTION DEVICES AND METHODS OF FORMING SAME

[75] Inventors: Cary D. Perttunen, Shelby Township, Mich.; William L. Reber, Schaumburg, Ill.

[73] Assignee: Motorola, Inc., Schaumburg, Ill.

[21] Appl. No.: 08/846,975

[22] Filed: Apr. 30, 1997

[51] Int. Cl.$^6$ ........................................................ C12Q 1/00
[52] U.S. Cl. .................................. 435/4; 435/6; 435/91.1; 435/91.2; 435/287.1; 435/287.2; 427/2; 436/518; 436/524; 436/525; 436/527; 436/806
[58] Field of Search ............................... 435/4, 6, 287.1, 435/287.2, 91.1, 91.2; 427/2; 436/518, 524, 525, 527, 806

[56] References Cited

U.S. PATENT DOCUMENTS

| | | |
|---|---|---|
| 4,118,280 | 10/1978 | Charles et al. . |
| 5,096,670 | 3/1992 | Harris et al. . |
| 5,139,744 | 8/1992 | Kaualski . |
| 5,518,923 | 5/1996 | Berndt et al. . |
| 5,532,128 | 7/1996 | Eggers et al. ............................. 435/16 |
| 5,565,324 | 10/1996 | Still et al. . |
| 5,653,939 | 8/1997 | Hollis et al. ............................. 422/50 |
| 5,736,332 | 4/1998 | Mandeki ................................. 435/6 |

OTHER PUBLICATIONS

Press, et al., "Random Numbers," *Numerical Recipes in C: The Art of Scientific Computing*: Cambridge University Press, Second Edition, 1992 (pp. 274–287).

*Primary Examiner*—Christopher L. Chin
*Assistant Examiner*—Jennifer Graser
*Attorney, Agent, or Firm*—Jeffrey G. Toler; James E. Gauger

[57] ABSTRACT

A molecular detection device including a support member (36) and a plurality of molecular receptors (34) arranged at a plurality of sites of the support member (36). In a first aspect, the molecular receptors (34) are arranged in accordance with a mapping selected from the group consisting of a random mapping and a pseudorandom mapping. In a second aspect, data associated with the mapping is written to a member associated with the support member (36). In a third aspect, the molecular receptors (34) includes a first plurality of molecular receptors germane to an application and at least one molecular receptor extraneous to the application.

29 Claims, 4 Drawing Sheets

FIG. 5

| RECEPTOR 1 | RECEPTOR 2 | RECEPTOR 3 | RECEPTOR 4 |
|---|---|---|---|
| RECEPTOR 5 | RECEPTOR 6 | RECEPTOR 7 | RECEPTOR 8 |
| RECEPTOR 9 | RECEPTOR 10 | RECEPTOR 11 | RECEPTOR 12 |
| RECEPTOR 13 | RECEPTOR 14 | RECEPTOR 15 | RECEPTOR 16 |

FIG. 6

| RECEPTOR 11 | RECEPTOR 2 | RECEPTOR 3 | RECEPTOR 4 |
|---|---|---|---|
| RECEPTOR 5 | RECEPTOR 6 | RECEPTOR 7 | RECEPTOR 8 |
| RECEPTOR 9 | RECEPTOR 10 | RECEPTOR 1 | RECEPTOR 12 |
| RECEPTOR 13 | RECEPTOR 14 | RECEPTOR 15 | RECEPTOR 16 |

FIG. 7

| RECEPTOR 11 | RECEPTOR 4 | RECEPTOR 3 | RECEPTOR 2 |
|---|---|---|---|
| RECEPTOR 5 | RECEPTOR 6 | RECEPTOR 7 | RECEPTOR 8 |
| RECEPTOR 9 | RECEPTOR 10 | RECEPTOR 1 | RECEPTOR 12 |
| RECEPTOR 13 | RECEPTOR 14 | RECEPTOR 15 | RECEPTOR 16 |

FIG. 8

| RECEPTOR 11 | RECEPTOR 4 | RECEPTOR 16 | RECEPTOR 2 |
|---|---|---|---|
| RECEPTOR 5 | RECEPTOR 6 | RECEPTOR 7 | RECEPTOR 8 |
| RECEPTOR 9 | RECEPTOR 10 | RECEPTOR 11 | RECEPTOR 12 |
| RECEPTOR 13 | RECEPTOR 14 | RECEPTOR 15 | RECEPTOR 3 |

FIG. 9

| RECEPTOR 2 | RECEPTOR 13 | RECEPTOR 9 | RECEPTOR 14 |
|---|---|---|---|
| RECEPTOR 12 | RECEPTOR 6 | RECEPTOR 3 | RECEPTOR 5 |
| RECEPTOR 10 | RECEPTOR 1 | RECEPTOR 16 | RECEPTOR 15 |
| RECEPTOR 4 | RECEPTOR 11 | RECEPTOR 8 | RECEPTOR 7 |

MOLECULAR DETECTION DEVICES AND
METHODS OF FORMING SAME

RELATED APPLICATIONS

The present application is related to the following applications:

"Method and System for Synthesizing Oligonucleotides Using Nucleotide-Specific Dispensing Bars", having Ser. No. 08/634,082, filed Apr. 17, 1996; now U.S. Pat. No. 5,733,509.

"Methods and Systems for Biological Reagent Placement", having Ser. No. 08/648,635, filed May 13, 1996, now U.S. Pat. No. 5,731,152.

The subject matter of the above-identified related applications is hereby incorporated by reference into this application.

TECHNICAL FIELD

The present invention relates to molecular detection devices.

BACKGROUND OF THE INVENTION

An increased effort has been directed toward developing chips for molecular detection. A typical molecular detection chip includes a substrate on which an array of recognition sites, binding sites, or hybridization sites is arranged. Each site has a respective molecular receptor which binds or hybridizes with a molecule having a predetermined structure.

A sample solution is applied to the molecular detection chip, and molecules in the sample bird or hybridize at one or more of the sites. The sites at which binding occurs are detected, and one or more molecular structures within the sample are subsequently deduced.

Of particular interest are DNA chips for sequencing and diagnostic applications. A DNA chip includes an array of binding sites each having single-stranded DNA probes or like synthetic probes for recognizing a respective DNA sequence. A sample of single-stranded DNA fragments, referred to as target DNA, is applied to the DNA chip. The DNA fragments attach to one or more of the probes. In sequencing applications, a sequence of nucleotide bases within the DNA fragment can be determined by detecting which probes have DNA fragments bound thereto. In diagnostic applications, a genomic sample from an individual is screened with respect to predetermined set of probes to determine if the individual has a genetically-inherited disease or a genetic predisposition to a disease.

The prospect of determining an individual's predisposition to disease based on his/her genome has led to warnings of a potential for genetic-based discrimination. For example, genetic information could be used to exclude high-risk individuals from health care either by denying health insurance coverage or by charging a prohibitive rate. The fear of discrimination may inhibit an individual from divulging his/her genetic status, even in light of the benefits of preventative measures and treatments which can be prescribed based on an early diagnosis of a genetic predisposition to a disease.

Accordingly, there is a need for a molecular detection devices and methods that provide increased security with respect to genetic information.

BRIEF DESCRIPTION OF THE DRAWINGS

The invention is pointed out with particularity in the appended claims. However, other features of the invention are disclosed in the following detailed description and the accompanying drawings in which:

FIG. 5 is a block diagram of an initial mapping of a plurality of molecular receptors to a plurality of sites;

FIG. 6 is a block diagram of a first intermediate mapping of the molecular receptors to the sites;

FIG. 7 is a block diagram of a second intermediate mapping of the molecular receptors to the sites;

FIG. 8 is a block diagram of a third intermediate mapping of the molecular receptors to the sites;

FIG. 9 is a block diagram of a final mapping of the molecular receptors to the sites;

DETAILED DESCRIPTION OF A PREFERRED EMBODIMENT

Embodiments of the present invention provide a molecular detection device having an arrangement of molecular receptors which is concealed or obscured. As a result, molecular structures in a sample applied to the molecular detection device are obscured or concealed with knowledge of hybridization information alone. To deduce the molecular structures in the sample, the hybridization information is processed in conjunction with data indicating the arrangement of the molecular receptors. The data can be stored in a member retained by an end user to restrict the ability of others to deduce the molecular structures in the sample. Alternatively, the data can be stored in a database that provides limited access thereto.

Figure 1:
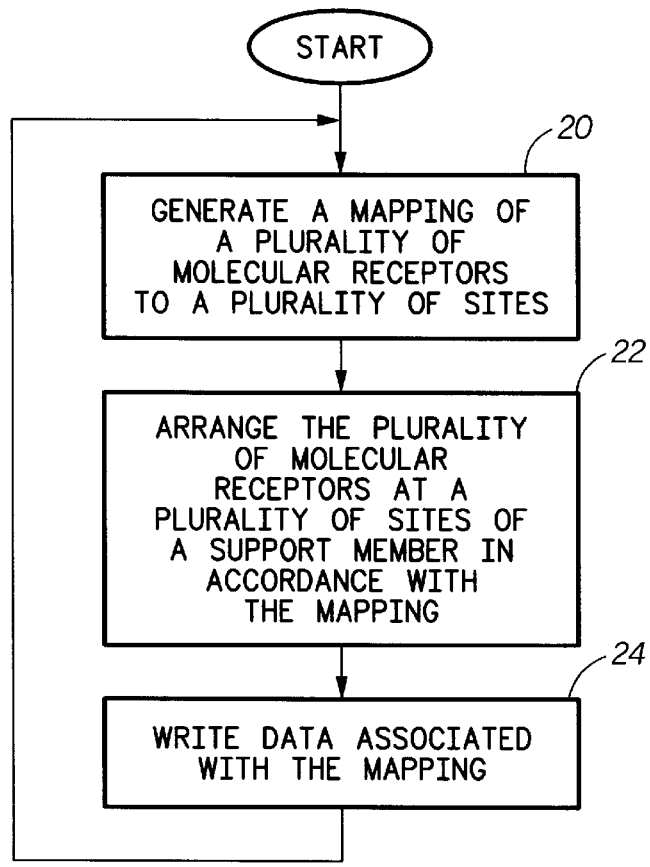
FIG. 1 is a flow chart of an embodiment of a method of forming at least one molecular detection device.

FIG. 1 is a flow chart of an embodiment of a method of forming at least one molecular detection device. As indicated by block 20, the method includes a step of generating a mapping of a plurality of molecular receptors to a plurality of sites of a support member. The mapping assigns each of the plurality of molecular receptors to a corresponding one of the plurality of sites.

Preferably, the mapping includes a pseudorandom mapping, i.e., a mapping produced by a pseudorandom process. The term "pseudorandom" describes entities that are selected by a definite computational process, but that satisfy one or more standard tests for statistical randomness. Hence, the pseudorandom mapping assigns the plurality of molecular receptors to the plurality of sites in a statistically-random manner using a definite computational process.

As an alternative to a pseudorandom mapping, the mapping can include a random mapping produced by a random process. The random process can include a physical random process such as a noise process in an electrical component such as a resistor or a semiconductor junction. The mapping is determined based upon observed or measured quantities of the physical random process, e.g. a voltage or a current in the electrical component.

Regardless of the type of mapping, it is preferred that the mapping conceals or obscures the identity of the molecular receptors at the sites. The use of a pseudorandom mapping or a random mapping is advantageous in making the mapping nonpredictable by others.

As indicated by block 22, the method includes a step of arranging the plurality of molecular receptors at the plurality of sites of the support member in accordance with the mapping. This step can include forming, transporting, positioning, placing, and/or depositing the plurality of molecular receptors to the plurality of sites in accordance with the mapping.

As indicated by block 24, the method includes a step of writing data associated with the mapping. The data can be written to the support member, a member associated with the support member, and/or to a computer database. Examples of the data written in this step include, but are not limited to, data which indicates the mapping and an identification code which identifies the mapping.

The steps indicated by blocks 20, 22, and 24 are performed to form a first molecular detection device having a first mapping of the molecular receptors to the sites. Thereafter, flow of the method is directed back to block 20 to generate a second mapping of the molecular receptors to the sites. Preferably, the second mapping differs from the first mapping and is statistically uncorrelated to the first mapping or statistically unpredictable given the first mapping.

The step indicated by block 22 is performed to form a second molecular detection device having the second mapping of the molecular receptors to sites supported by a support member. The step indicated by block 24 is performed to write data associated with the second mapping to either the support member for the second molecular detection device, a member associated with the support member, and/or to the computer database.

Thereafter, the steps indicated by blocks 20, 22, and 24 further can be repeated to form any plurality of molecular detection devices. Preferably, the plurality of molecular detection devices have mappings which are statistically uncorrelated and/or statistically independent.

Figure 2:
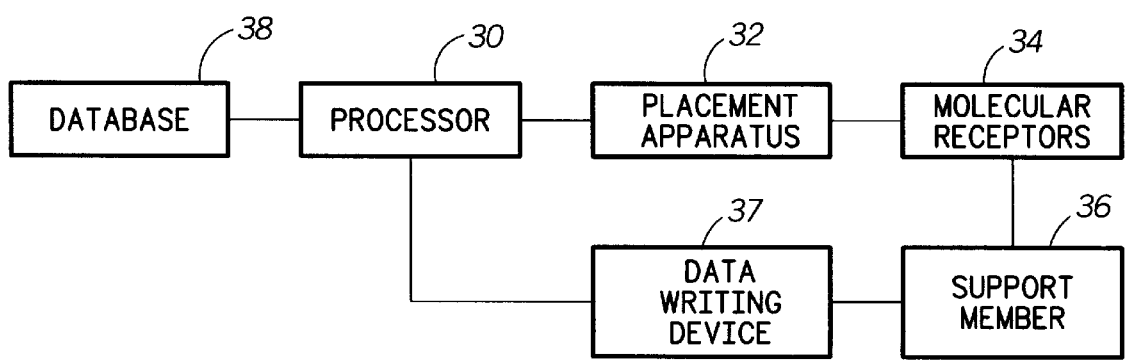
FIG. 2 is a block diagram of an embodiment of a system for forming at least one molecular detection device.

FIG. 2 is a block diagram of an embodiment of a system for forming at least one molecular detection device. The system performs the steps described with reference to FIG. 1 to form the at least one molecular detection device, and preferably, to form a plurality of molecular detection devices. The system can further perform other steps described with reference to other figures in the present application.

The system includes a processor 30 which generates mappings of molecular receptors to sites of a molecular detection device. The processor 30 can include a computer or like processing apparatus to generate the mappings. The processor 30 further directs the operation of other system components to produce the at least one molecular detection device. The processor 30 receives instructions for generating the mappings and for directing the operation of the system from an article such as a computer-readable storage medium having computer-readable data stored therein. Examples of the computer-readable storage medium include, but are not limited to, a logic circuit, a memory, a mass storage medium, an optical disk, a CD-ROM, a magnetic disk, a floppy disk, a hard disk, and a PCMCIA card.

A placement apparatus 32 receives a signal indicative of a mapping from the processor 30. The placement apparatus 32 arranges a plurality of molecular receptors 34 to a plurality of sites of a support member 36 in accordance with the mapping. Examples of the placement apparatus 32 are given in the copending applications entitled "Method and System for Synthesizing Oligonucleotides Using Nucleotide-Specific Dispensing Bars" and "Methods and Systems for Biological Reagent Placement" which are incorporated by reference into the present disclosure. In another embodiment, the placement apparatus 32 includes a robotic placement apparatus such as a liquid handling robot.

Each of the molecular receptors 34 is for binding or hybridizing with a corresponding molecule having a predetermined structure. Each molecular receptor 34 can include biological molecules or synthetic molecules having a specific affinity to its corresponding molecule. For example, each molecular receptor 34 can include a chain of at least one nucleotide to hybridize with a molecule having a complementary chain of at least one nucleotide. Here, each molecular receptor 34 can include a DNA probe for detecting a corresponding, complementary DNA sequence in a sample, or an RNA probe for detecting a corresponding, complementary RNA sequence in a sample. In another example, each molecular receptor 34 can include an antigen having an affinity to an antibody.

As another alternative, each molecular receptor 34 can include a member, such as a film, having an affinity to a corresponding molecule. For example, each film can be molecularly imprinted in accordance with U.S. Pat. No. 5,587,273 to Yan et al., which is hereby incorporated by reference into this disclosure. In this case, each film is molecularly imprinted using a corresponding imprinting molecule. Other examples of molecular receptors are given in U.S. Pat. Nos. 5,110,833, 5,461,175, 5,453,199, 5,310,648, 5,541,342, and 5,372,719, which are hereby incorporated by reference into the present disclosure. Examples of molecules which can be detected by the molecular receptors 34 include, but are not limited to, polynucleotides, pathogens, proteins, and enzymes.

The support member 36 can include a substrate which supports the molecular receptors 34. The substrate can be formed of various materials including semiconductive materials, conductive materials, and dielectric materials. Examples of materials include but are not limited to silicon, glass, metals, polymers and plastics.

The support member 36 or the substrate defines a plurality of sites for receiving the molecular receptors 34 on its surface. The plurality of sites can have any arrangement on the surface. In a preferred embodiment, the sites are arranged as a two-dimensional array on the surface. The molecular receptors 34 can be bound to the surface using a primer, a gel, or an adhesive, or can be integrated with the surface using a molecular imprinting approach. Alternatively, like ones of the molecular receptors 34 can be supported by a corresponding member to be placed on the surface. For example, molecular receptors 34 can be contained in a prepatterned gel member which is placed at a position of the surface dependent upon the mapping.

A data writing device 37 receives a signal associated with the mapping from the processor 30. The data writing device 37 writes data associated with the mapping directly to the support member 36 or to another member associated with the support member 36. The data can include data which indicates or encodes the mapping, and/or data which identifies the mapping. Examples of the data writing device 37 include, but are not limited to: (i) a magnetic writing head to write magnetic data to a magnetic storage medium; (ii) a printing device to write printed data to a substrate; (iii) an electronic writing device to write electronic data to an electronic storage device such as a memory; and (iv) an optical writing device to write optical data to an optical storage medium.

Optionally, the system includes a database 38 which receives a signal associated with the mapping from the processor 30. The signal can include an identification code for the mapping and/or data indicative of the mapping. The database 38 stores the identification code and/or the data for the molecular detection device.

Preferably, the database 38 stores a plurality of identification codes and/or data for a plurality of molecular detection devices. The database 38 is accessed to deduce molecular structures in a sample applied to a molecular detection device produced by the system. Access to the database 38 can be limited to limit which individuals can deduce information from results generated by the molecular detection device.

Figure 3:
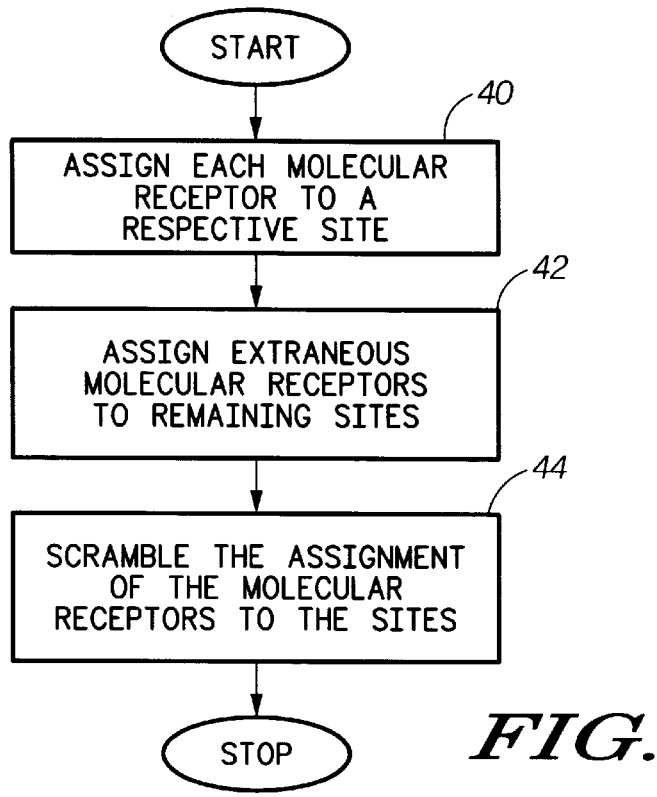
FIG. 3 is a flow chart of an embodiment of a method of generating a mapping of a plurality of molecular receptors to a plurality of sites.

FIG. 3 is a flow chart of an embodiment of a method of generating a mapping of a plurality of molecular receptors to a plurality of sites. The plurality of molecular receptors can include a first plurality of molecular receptors germane to an application of the molecular detection device and a second plurality of molecular receptors which may or may not be germane to the application. Preferably, the second plurality of molecular receptors includes at least one extraneous molecular receptor which is not germane to the application. The at least one extraneous molecular receptor is beneficial in obscuring binding information generated by the molecular detection device.

As indicated by block 40, the method includes a step of assigning each of the first plurality of molecular receptors to a respective one of the sites. The first plurality of molecular receptors can comprise molecular receptors which are to be included in each of a plurality of molecular detection devices.

As indicated by block 42, the method optionally includes a step of assigning a second plurality of molecular receptors to remaining ones of the sites. This step can include steps of randomly or pseudorandomly generating or selecting at least one extraneous molecular receptor to include in the second plurality of molecular receptors. For example, a random or pseudorandom chain of at least one nucleotide can be generated to form an extraneous molecular receptor that is receptive to a random or a pseudorandom sequence complementary to the at least one nucleotide. Alternatively, a molecular receptor can be randomly or pseudorandomly selected from a preselected group of molecular receptors. Preferably, the at least one extraneous molecular receptor differs for each of a plurality of molecular detection devices.

As indicated by block 44, the method includes a step of scrambling the assignment of the molecular receptors, including the first plurality and the second plurality of molecular receptors, to the sites. The assignment can be scrambled using a deterministic process, a random process, or a pseudorandom process as subsequently described herein.

Figure 4:
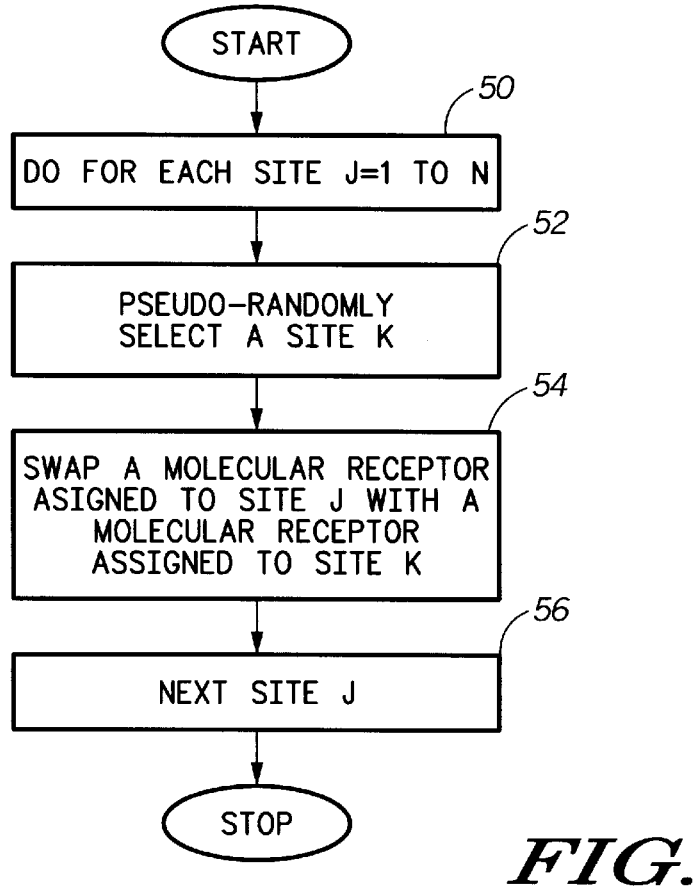
FIG. 4 is a flow chart of an embodiment of a method of scrambling the assignment of a plurality of molecular receptors to a plurality of sites.

FIG. 4 is a flow chart of an embodiment of a method of scrambling the assignment of a plurality of molecular receptors to a plurality of sites. Each of the plurality of sites is identified by an integer from 1 to N, where N denotes the total number of sites being scrambled.

As indicated by block 50, the method includes a step of looping through steps for each of the N sites. A current site of the N sites being considered in the loop is denoted using an indexing variable J.

As indicated by block 52, the method includes a step of randomly or pseudorandomly selecting one of the plurality of sites. The randomly-selected or pseudorandomly-selected site is referred to as site K. Preferably, this step includes a step of generating a pseudorandom integer K between 1 and N, inclusive. Further, it is preferred that the pseudorandom integer K be uniformly distributed between 1 and N, inclusive. Hence, the probability or the relative frequency of selecting each integer between 1 and N is 1/N. Various computer-implemented pseudorandom number generating methods can be utilized in this step. Alternatively, a randomly-generated integer between 1 and N can be generated.

As indicated by block 54, the method includes a step of swapping a molecular receptor assigned to site J with a molecular receptor assigned to site K. In other words, the molecular receptor assigned to site J is reassigned to site K and the molecular receptor assigned to site K is reassigned to site J.

As indicated by block 56, the index variable J is incremented and flow of the method is directed back to block 52 until J is equal to N. As a result, the steps indicated by blocks 52, 54, and 56 are performed N times, once for each of the sites, to scramble the assignment. If desired, the above-described method can be repeatedly performed to further scramble the assignment.

FIG. 5 is a block diagram of an initial mapping of a plurality of molecular receptors to a plurality of sites. For purposes of illustration, sixteen sites are considered, although any number of sites can be considered in general. Sixteen molecular receptors, indicated by RECEPTOR1 to RECEPTOR16, are illustrated. Each of the sixteen molecular receptors is assigned to a corresponding one of the sixteen sites.

Each of the sites is identified by a unique integer from 1 to 16. For purposes of illustration and without loss of generality, the integer for identifying the site is given by the receptor number in the initial mapping. Hence, site 1 identifies a site indicated by reference numeral 60, site 2 identifies a site indicated by reference numeral 62, site 3 identifies a site indicated by reference numeral 64, etc., up to site 16 identifying a site indicated by reference numeral 66.

The initial mapping is generated by the steps indicated by blocks 40 and 42 described with reference to FIG. 3. For purposes of illustration and example, the sixteen molecular receptors include two molecular receptors for identifying predispositions to two diseases from a genomic sample, and fourteen extraneous molecular receptors for concealing or obscuring the predisposition information.

FIG. 6 is a block diagram of a first intermediate mapping of the molecular receptors to the sites. The first intermediate mapping results from a first iteration of the loop described with reference to FIG. 4 using the initial mapping given in FIG. 5.

In the first iteration of the loop, the indexing variable J has a value of one. For purposes of illustration, site 11 (indicated by reference numeral 70) is pseudorandomly selected from the sixteen sites in the step indicated by block 52. The molecular receptor in site 1, namely RECEPTOR1, is swapped with the molecular receptor in site 11, namely RECEPTOR11 by the step indicated by block 54. Hence, RECEPTOR11 is assigned to site 1 (reference numeral 60) and RECEPTOR1 is assigned to site 11 (reference numeral 70) in the first intermediate mapping.

FIG. 7 is a block diagram of a second intermediate mapping of the molecular receptors to the sites. The second intermediate mapping results from a second iteration of the loop described with reference to FIG. 4 using the first intermediate mapping given in FIG. 6.

In the second iteration of the loop, the indexing variable J is equal to two. For purposes of illustration, site 4 (indicated by block 72) is pseudorandomly selected from the sixteen sites in the step indicated by block 52. The molecular receptor in site 2, namely RECEPTOR2, is swapped with the molecular receptor in site 4, namely RECEPTOR4 by the step indicated by block 54. Hence, RECEPTOR4 is assigned to site 2 (reference numeral 62) and RECEPTOR2 is assigned to site 4 (reference numeral 72) in the second intermediate mapping.

FIG. 8 is a block diagram of a third intermediate mapping of the molecular receptors to the sites. The third intermediate mapping results from a third iteration of the loop described with reference to FIG. 4.

In the third iteration of the loop, the indexing variable J is equal to three. For purposes of illustration, site 16 (indicated by reference numeral 66) is pseudorandomly selected from the sixteen sites in the step indicated by block 52. The molecular receptor in site 3, namely RECEPTOR3, is swapped with the molecular receptor in site 16, namely RECEPTOR16 by the step indicated by block 54. Hence, RECEPTOR16 is assigned to site 3 (reference numeral 66) and RECEPTOR3 is assigned to site 16 (reference numeral 64) in the third intermediate mapping.

FIG. 9 is a block diagram of a final mapping of the molecular receptors to the sites. The final mapping results from performing sixteen iteration of the loop described with reference to FIG. 4. In the final mapping, each site has an equal probability of having any preselected molecular receptor of the sixteen molecular receptors assigned thereto. Similarly, each molecular receptor has an equal probability of being assigned to any preselected site of the sixteen sites. The final mapping is used to direct the arrangement of molecular receptors to the sites as described for block 22 in FIG. 1.

Figure 10:
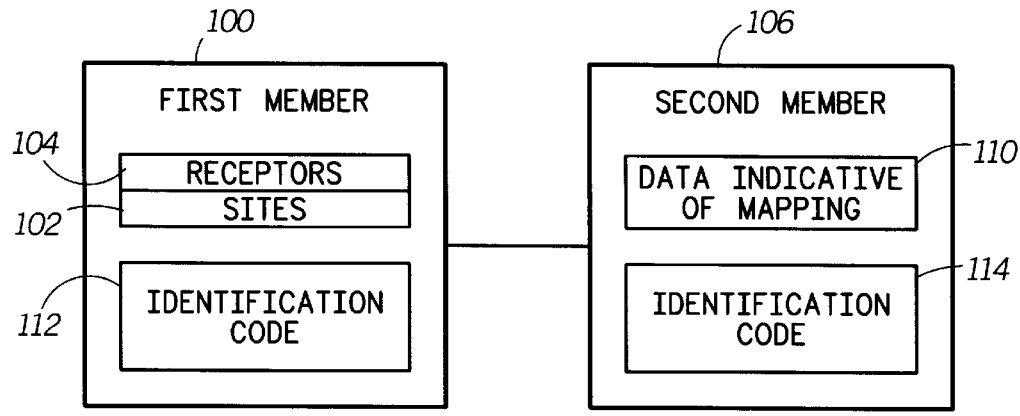
FIG. 10 is a block diagram of a molecular detection device in accordance with the present invention.

FIG. 10 is a block diagram of a molecular detection device in accordance with the present invention. The molecular detection device includes a first member 100 having a plurality of sites 102 for receiving and supporting a plurality of molecular receptors 104. The molecular receptors 104 are arranged in accordance with a mapping, such as the various mappings described herein.

A second member 106 is associated with the first member 100. The second member 106 can be attached to the first member 100, can support the first member 100, or can be included with the first member 100 in a package. Alternatively, the first member 100 and the second member 106 can be formed of a unitary member such as a single substrate.

The second member 106 supports data 110 indicative of the mapping of the molecular receptors 104 to the sites 102. The data 110 can encode an array which indicates the molecular receptor at each site. Alternatively, the data 110 can encode how an initial mapping of molecular receptors to sites is scrambled to form the final mapping of the molecular receptors 104. Here, the data 110 can encode a pseudorandom sequence used to scramble the initial mapping. For example, the data 110 can encode a pseudorandom sequence of integers, such as the one described with reference to FIGS. 5 to 9 (namely, 11, 4, 16, etc.), used to scramble an initial mapping using the method described with reference to FIG. 4.

The data 110 can be stored electronically such as by an electronic memory, magnetically such as by a magnetic storage medium, or optically such as by an optical storage medium so as to be machine-readable. Alternatively, the data 110 can include printed data such as a bar code. The bar code can include a one-dimensional bar code or a two-dimensional bar code.

Optionally, the first member 100 can support data 112 indicative of an identification code. Similarly, the second member 106 can support data 114 indicative of the identification code. The identification code identifies the mapping of the molecular receptors 104 to the sites 102 without revealing the mapping. For example, the identification code can identify a record in a database, such as the database 38 described with reference to FIG. 2, having the data indicative of the mapping stored therein. The identification code can include a series of letters, numbers, or characters, which can be read by a human. Alternatively, the identification code can be stored as machine-readable data in a manner similar to the data 110.

Figure 11:
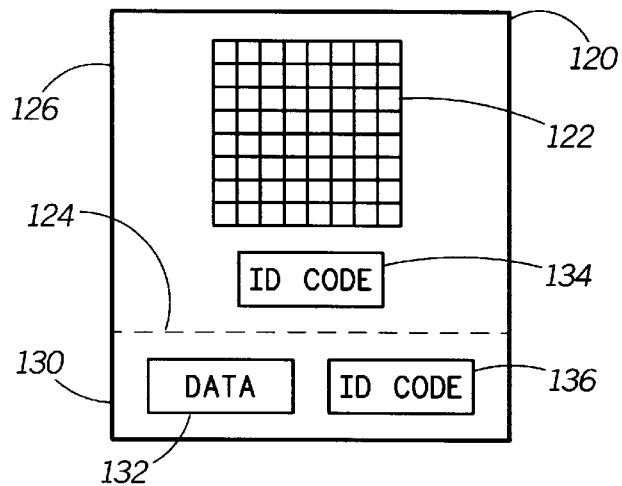
FIG. 11 is a schematic block diagram of a first embodiment of a molecular detection device.

FIG. 11 is a schematic block diagram of a first embodiment of a molecular detection device. The molecular detection device includes a substrate 120 which supports a molecular detection array 122. For purposes of illustration, the molecular detection array 122 includes sixty-four binding sites arranged as an 8×8 array.

Located at each binding site is a respective oligonucleotide receptor. For example, each binding site can have a receptor for a corresponding three-base DNA sequence. Here, the molecular detection array 122 has molecular receptors for all sixty-four three-base sequences of single-stranded DNA. The molecular receptors are arranged at the sixty-four binding sites in accordance with a random mapping or a pseudorandom mapping.

The substrate 120 includes a perforation 124 which demarcates a first portion 126 from a second portion 130. Data 132 indicative of the mapping is supported by the second portion 130.

In use, the second portion 130 is separated from the first portion 126 along the perforation 124 prior to applying a sample to the molecular detection array 122. An end user retains the second portion 130 for safekeeping.

The sample is applied to the molecular detection array 122. Molecules in the sample bind or hybridize at one or more of the sites. Thereafter, particular sites at which hybridization occurs are detected, and data representative of the hybridization results are stored.

Advantageously, one or more molecular structures in the sample are unidentifiable based on the hybridization results alone, i.e. without knowledge of the mapping. By retaining the second portion 130 having the data 132 indicative of the mapping, the end user restricts the ability of others to deduce molecular structures in the sample based on the hybridization results.

Optionally, the first portion 126 supports an identification code 134 and the second portion 130 supports an identical identification code 136. The identification codes 134 and 136 aid in verifying that the first portion 126 and the second portion 130, when separated, are for the same device. The identification codes 134 and 136 include a series of human-readable printed characters or a machine-readable bar code, for example.

Figure 12:
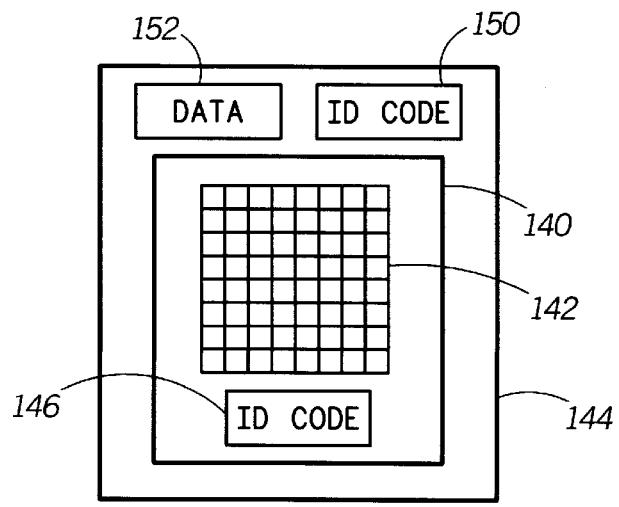
FIG. 12 is a schematic block diagram of a second embodiment of a molecular detection device.

FIG. 12 is a schematic block diagram of a second embodiment of a molecular detection device. The molecular detection device includes a substrate 140 which supports a molecular detection array 142 as described with reference to FIG. 11.

The substrate 140 is supported by a second substrate 144. The second substrate 144 provides a backing portion of a package to contain the substrate 144. After opening the package, the substrate 140 is removed to become dissociated with the second substrate 144. Thereafter, a sample can be applied to the molecular detection array 142 to generate a set of hybridization results as described with reference to FIG. 11.

Optionally, the substrate 140 supports an identification code 146 and the second substrate 144 supports an identical identification code 150. The identification codes 146 and 150 verify that the substrate 140 is associated with the second substrate 144. The second substrate 144 further supports data 152 indicative of the mapping.

Although described in detail for use with hybridization arrays, it is noted that the teachings herein can be applied to other molecular detection devices such as electrophoresis devices and combinatorial arrays. For an electrophoresis device, the sites comprise electrophoresis lanes or filling wells therefor. Samples formed by a restriction analysis are mapped to the electrophoresis lanes in accordance with any of the various mappings described herein. Extraneous samples can be formed using randomly-selected or pseudorandomly-selected restriction enzymes applied to a sample.

In addition to the herein-described applications, embodiments of the molecular detection device are amenable for use in forensic applications, paternity tests, identification from human remains, and rapist identification. In these applications, a first sample from an individual is applied to a first molecular detection device to form a first identity signature. A second sample from either a crime scene, a child whose paternity is in question, human remains, or a rape victim is applied to a second molecular detection device to form a second identity signature.

Preferably, the first molecular detection device has a first mapping which is nonpredictable to a party generating the second identity signature, and the second molecular detection device has a second mapping which is nonpredictable to a party generating the first identity signature. A measure of correlation between the first identity signature and the second identity signature can be determined based upon the first mapping and the second mapping. If desired, the measure of correlation can be determined and displayed using a computer system without revealing either mapping or either unscrambled identity signature. Further, the measure of correlation can be determined and displayed only for a limited number of pairs of identity signatures (e.g. only for a single pair of identity signatures). By not revealing an unscrambled identity signature, the potential for repeatedly performing tests until a desired outcome (e.g. a desired identity signature) is produced is reduced.

Thus, there has been described herein several embodiments including preferred embodiments of molecular detection devices and methods of forming same.

Because the various embodiments of the present invention have a plurality of molecular receptors arranged at a plurality of sites in accordance with a random mapping or a pseudorandom mapping, they provide a significant improvement in concealing or obscuring the arrangement from others.

Additionally, the various embodiments of the present invention as herein-described write data indicative of the arrangement to a member for safekeeping by an end user. The end user allows an individual to deduce information based on binding results by providing the member to the individual. The end user inhibits an individual to deduce the information by withholding the member from the individual.

Further, the various embodiments of the present invention include at least one extraneous molecular receptor not germane to applications of interest. The at least one extraneous molecular receptor is advantageous in obscuring information generated in a test.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A method of forming a molecular detection device, the method comprising the steps of:
   arranging and immobilizing a plurality of molecular receptors at a plurality of sites of a support member, the plurality of molecular receptors arranged in accordance with a pseudorandom mapping wherein the mapping is stored in a memory device.

2. The method of claim 1 further comprising the step of generating the pseudorandom mapping of the plurality of molecular receptors to the plurality of sites.

3. The method of claim 2 wherein the step of generating the pseudorandom mapping includes scrambling an initial assignment of the plurality of molecular receptors to the plurality of sites.

4. The method of claim 1 wherein each molecular receptor of the plurality of molecular receptors has an equal probability of being assigned to any preselected site of the plurality of sites.

5. The method of claim 1 wherein each site of the plurality of sites has an equal probability of being assigned any preselected molecular receptor of the plurality of molecular receptors.

6. The method of claim 1 wherein the mapping is statistically uncorrelated with a second mapping for a second molecular detection device.

7. A molecular detection device comprising:
   a support member; and
   a plurality of molecular receptors arranged and immobilized at a plurality of sites of the support member, the plurality of molecular receptors arranged in accordance with a pseudorandom mapping wherein the pseudorandom mapping is statistically uncorrelated with a second pseudorandom mapping for a second molecular detection device.

8. The molecular detection device of claim 7 wherein each molecular receptor of the plurality of molecular receptors has an equal probability of being assigned to any preselected site of the plurality of sites.

9. The molecular detection device of claim 7 wherein each site of the plurality of sites has an equal probability of being assigned any preselected molecular receptor of the plurality of molecular receptors.

10. A method of forming a molecular detection device, the method comprising the steps of:
    arranging a plurality of molecular receptors at a plurality of sites of a support member, the plurality of molecular receptors arranged in accordance with a pseudorandom mapping; and
    writing data associated with the pseudorandom mapping to a member associated with the support member.

11. The method of claim 10 wherein the member is attached to the support member.

12. The method of claim 10 wherein the member is detachable from the support member.

13. The method of claim 10 wherein the data includes an identification code which identifies the pseudorandom mapping.

14. The method of claim 10 wherein the data encodes the pseudorandom mapping.

15. The method of claim 14 wherein the data includes a sequence of integers to encode the pseudorandom mapping.

16. The method of claim 10 further comprising the step of writing data associated with the pseudorandom mapping to a database.

17. The method of claim 10 wherein the data is selected from the group consisting of printed data, magnetic data, electronic data, and optical data.

18. A molecular detection device comprising:

a support member having a member associated therewith;

a plurality of molecular receptors at a plurality of sites of the support member, the plurality of molecular receptors arranged in accordance with a pseudorandom mapping; and data associated with the pseudorandom mapping written to the member.

19. The molecular detection device of claim 18 wherein the data includes an identification code which identifies the pseudorandom mapping.

20. A method of forming a molecular detection device for an application, the method comprising the steps of:

pseudorandomly selecting at least one molecular receptor extraneous to the application from a plurality of extraneous molecular receptors; and arranging a plurality of molecular receptors at a plurality of sites of a support member, the plurality of molecular receptors including at least one molecular receptor germane to the application and the at least one molecular receptor extraneous to the application to assist in concealing a result of the application.

21. A method of forming a molecular detection device for an application, the method comprising the steps of:

pseudorandomly generating at least one molecular receptor extraneous to the application; and arranging a plurality of molecular receptors at a plurality of sites of a support member, the plurality of molecular receptors including at least one molecular receptor germane to the application and the at least one molecular receptor extraneous to the application to assist in concealing a result of the application.

22. The method of claim 20 wherein the plurality of molecular receptors are arranged in accordance with a pseudorandom mapping.

23. The method of claim 20 wherein each of the plurality of molecular receptors is receptive to a respective chain of at least one nucleotide.

24. A molecular detection device comprising:

a support member; and a plurality of molecular receptors arranged at a plurality of sites of the support member, the plurality of molecular receptors including at least one molecular receptor germane to an application and at least one pseudorandomly-selected molecular receptor extraneous to the application to assist in concealing a result of the application.

25. The molecular detection device of claim 24 wherein the at least one pseudorandomly-selected molecular receptor is receptive to a pseudorandom sequence of at least one nucleotide.

26. The molecular detection device of claim 24 wherein each of the plurality of molecular receptors is receptive to a respective chain of at least one nucleotide.

27. The molecular detection device of claim 18 wherein the plurality of molecular receptors are immobilized at the plurality of sites.

28. The molecular detection device of claim 18 wherein the data encodes the pseudorandom mapping.

29. The molecular detection device of claim 28 wherein the data includes a sequence of integers to encode the pseudorandom mapping.

* * * * *